(12) United States Patent
Rummery et al.

(10) Patent No.: US 11,944,754 B2
(45) Date of Patent: Apr. 2, 2024

(54) AIR DELIVERY CONDUIT

(71) Applicant: RESMED PTY LTD, Bella Vista (AU)

(72) Inventors: Gerard Michael Rummery, Woodford (AU); James Morrison, Thornleigh (AU); Robert John King, Wentworth Point (AU); Justin John Formica, Voyager Point (AU)

(73) Assignee: ResMed Pty Ltd, Bella Vista (AU)

( * ) Notice: Subject to any disclaimer, the term of this patent is extended or adjusted under 35 U.S.C. 154(b) by 0 days.

(21) Appl. No.: 18/101,618

(22) Filed: Jan. 26, 2023

(65) Prior Publication Data

US 2023/0166069 A1 Jun. 1, 2023

Related U.S. Application Data

(60) Continuation of application No. 16/912,857, filed on Jun. 26, 2020, now Pat. No. 11,565,071, which is a
(Continued)

(30) Foreign Application Priority Data

Mar. 15, 2011 (AU) .................. 2011900911

(51) Int. Cl.
| | |
|---|---|
| *F16L 11/00* | (2006.01) |
| *A61M 16/06* | (2006.01) |
| *A61M 16/08* | (2006.01) |
| *D03D 15/56* | (2021.01) |
| *F16L 11/112* | (2006.01) |
| *F16L 11/115* | (2006.01) |
| *B33Y 80/00* | (2015.01) |

(52) U.S. Cl.
CPC .... *A61M 16/0875* (2013.01); *A61M 16/0633* (2014.02); *A61M 16/0683* (2013.01); *D03D 15/56* (2021.01); *F16L 11/112* (2013.01); *F16L 11/115* (2013.01); *A61M 2205/02* (2013.01); *B33Y 80/00* (2014.12); *D10B 2509/00* (2013.01)

(58) Field of Classification Search
CPC .......... A61M 16/0875; A61M 16/0635; A61M 16/0633; A61M 16/0683; F16L 11/112; F16L 11/115
USPC .... 128/206.21; 138/121, 122, 125, 129, 171
See application file for complete search history.

(56) References Cited

U.S. PATENT DOCUMENTS

| | | |
|---|---|---|
| 2,260,816 A | 10/1941 | Albin |
| 2,396,059 A | 3/1946 | Thomas |

(Continued)

FOREIGN PATENT DOCUMENTS

| | | |
|---|---|---|
| CN | 101687085 A | 3/2010 |
| EP | 0 009 402 | 4/1980 |

(Continued)

OTHER PUBLICATIONS

Extended European Search Report dated Feb. 2, 2023, in related EP Application No. 20756702.5 (8 pages).
(Continued)

*Primary Examiner* — David R Deal
(74) *Attorney, Agent, or Firm* — Nixon & Vanderhye P.C.

(57) ABSTRACT

A mask system and an air delivery conduit for use in the treatment of respiratory disorders. The air delivery conduit may comprise a textile having an airtight arrangement. A support structure may be provided to the conduit to provide form.

21 Claims, 6 Drawing Sheets

Related U.S. Application Data continuation of application No. 15/599,889, filed on May 19, 2017, now Pat. No. 10,729,869, which is a division of application No. 14/005,094, filed as application No. PCT/AU2012/000269 on Mar. 15, 2012, now Pat. No. 9,656,038.

(56) References Cited

U.S. PATENT DOCUMENTS

| | | | |
|---|---|---|---|
| 2,813,573 A | 11/1957 | Roberts | |
| 2,897,840 A | 8/1959 | Roberts | |
| 3,037,798 A | 6/1962 | Cooper | |
| 3,163,707 A | 12/1964 | Darling | |
| 3,172,428 A * | 3/1965 | Tudge | F16L 11/10 29/454 |
| 3,205,913 A | 9/1965 | Sperry | |
| 3,234,970 A | 2/1966 | Baker et al. | |
| 3,288,170 A * | 11/1966 | Doyle | F16L 11/115 138/123 |
| 3,299,908 A | 1/1967 | Petzetakis | |
| 3,312,250 A | 4/1967 | Sirignano | |
| 3,513,668 A | 5/1970 | Mintz | |
| 3,747,374 A | 7/1973 | Meyer | |
| 3,812,885 A | 5/1974 | Sajben | |
| 3,857,415 A | 12/1974 | Morin | |
| 3,860,043 A * | 1/1975 | Kutnyak | F16L 43/008 285/236 |
| 4,175,992 A | 11/1979 | Grawey | |
| 4,224,463 A | 9/1980 | Koerber et al. | |
| 4,259,991 A | 4/1981 | Kutnyak | |
| 4,265,239 A | 5/1981 | Fischer, Jr. et al. | |
| 4,276,908 A | 7/1981 | Home | |
| 4,308,895 A | 1/1982 | Greco | |
| 4,357,962 A | 11/1982 | Shaw | |
| 4,405,341 A | 9/1983 | Jaschek | |
| 4,415,389 A | 11/1983 | Medford | |
| 4,478,661 A | 10/1984 | Lewis | |
| 4,553,568 A | 11/1985 | Piccoli | |
| 4,842,023 A | 6/1989 | Whitworth | |
| 4,929,478 A | 5/1990 | Conaghan et al. | |
| 5,232,429 A | 8/1993 | Cizek et al. | |
| 5,326,410 A | 7/1994 | Boyles | |
| 5,623,922 A | 4/1997 | Smith | |
| 5,640,951 A | 6/1997 | Huddart et al. | |
| 6,199,676 B1 | 3/2001 | Targiroff | |
| 6,227,094 B1 | 5/2001 | Taylor | |
| 6,508,276 B2 | 1/2003 | Radlinger | |
| 6,769,431 B2 | 8/2004 | Smith et al. | |
| 7,469,719 B2 | 12/2008 | Gray | |
| 7,926,517 B2 | 4/2011 | Horimoto | |
| 8,776,836 B2 | 7/2014 | Ragner et al. | |
| 9,656,038 B2 | 5/2017 | Rummery et al. | |
| 10,034,995 B2 | 7/2018 | Kooij | |
| 10,729,869 B2 | 8/2020 | Rummery | |
| 2001/0039972 A1 | 11/2001 | Badders | |
| 2001/0054422 A1 | 12/2001 | Smith | |
| 2003/0098084 A1 | 5/2003 | Ragner et al. | |
| 2003/0183294 A1 | 10/2003 | Carlson | |
| 2004/0045549 A1 | 3/2004 | Smith | |
| 2004/0065335 A1 | 4/2004 | Huber | |
| 2004/0079371 A1 | 4/2004 | Gray | |
| 2004/0194781 A1 | 10/2004 | Fukunaga | |
| 2005/0241644 A1 | 11/2005 | Gunaratnam et al. | |
| 2006/0165829 A1 | 7/2006 | Smith | |
| 2007/0207186 A1 | 9/2007 | Scanlon | |
| 2007/0267012 A1* | 11/2007 | McCarthy | B63C 11/18 128/201.27 |
| 2008/0173305 A1 | 7/2008 | Frater | |
| 2008/0178957 A1 | 7/2008 | Thomas | |
| 2008/0202620 A1 | 8/2008 | Van Hooren | |
| 2010/0018534 A1 | 1/2010 | Veliss et al. | |
| 2010/0224195 A1 | 9/2010 | Henry | |
| 2011/0016654 A1 | 1/2011 | Chudleigh | |
| 2011/0108031 A1 | 5/2011 | Korneff | |
| 2011/0303318 A1 | 12/2011 | Nicolas | |
| 2014/0007881 A1 | 1/2014 | Rummery et al. | |
| 2014/0010246 A1 | 4/2014 | Ovizinsky | |
| 2015/0352306 A1 | 12/2015 | Scheiner | |
| 2016/0296720 A1 | 10/2016 | Henry | |
| 2017/0252529 A1 | 9/2017 | Rummery et al. | |
| 2017/0333662 A1 | 11/2017 | Ovzinsky et al. | |
| 2018/0043120 A1 | 2/2018 | Hunley | |
| 2019/0015192 A1 | 1/2019 | Nakazawa | |
| 2020/0324069 A1 | 10/2020 | Rummery et al. | |

FOREIGN PATENT DOCUMENTS

| | | |
|---|---|---|
| EP | 2 039 386 B1 | 9/2008 |
| GB | 656352 | 8/1951 |
| GB | 1249566 | 10/1971 |
| JP | H06-254164 | 9/1994 |
| JP | 2001-336678 A | 12/2001 |
| JP | 2003-275228 | 9/2003 |
| JP | 2009-072596 | 4/2009 |
| JP | 2014-514035 A | 6/2014 |
| JP | 2014-167343 A | 9/2014 |
| JP | 2018-527156 A | 9/2018 |
| NZ | 162598 | 1/1971 |
| WO | WO 2005/075186 | 8/2005 |
| WO | WO 2007/109837 | 10/2007 |
| WO | 2012/122601 A1 | 9/2012 |
| WO | WO 2013/006913 A1 | 1/2013 |
| WO | WO 2017/213523 A1 | 12/2017 |
| WO | WO 2020/000033 A1 | 1/2020 |

OTHER PUBLICATIONS

Notice of Reasons for Rejection and English translation thereof dated Mar. 22, 2022 in corresponding JP application 2019-100282 (10 pages).
Pre-Appeal Examination Report and English translation thereof dated Nov. 8, 2021 in corresponding JP apglication 2019-100282 (6 pages).
Final Rejection and English translation thereof dated May 10, 2021 in corresponding JP application 2019-100282 (7 pages).
Further Examination Report dated Jan. 22, 2021 in corresponding NZ Application 756591 (2 pages).
First Examination Report dated Feb. 12, 2021 in corresponding NZ Application 772270 (3 pages).
Japanese Notice of Reasons for Rejection and English translation thereof dated Aug. 17, 2020 in corresponding JP Patent application 2019-100282.
International Search Report dated May 4, 2020 in related PCT application PCT/IB2020/051079.
Written Opinion dated May 4, 2020 in related PCT application PCT/IB2020/051079.
Definition of "polymer" from Wikipedia, from May 13, 2019, see www.en.wikipedia.org/wiki/Polymer.
JP Office Action and English translation thereof dated Apr. 27, 2020 in corresponding Japanese Application 2017-159153.
Written Opinion dated May 4, 2020 in related PCT Application PCT/IB2020/051079, citing US 2014/0102456, US 2017/0333662, US 2015/0352306, US 2017/0252529, WO 2017/213523, WO 2020/000033 and WO 2013/006913.
U.S. Office Action dated Nov. 26, 2019 in related U.S. Appl. No. 15/425,891.
JP Report on the Reexamination Prior to Trial and English translation thereof dated Aug. 5, 2019 and retrieved from the JPO database Aug. 19, 2019 in corresponding JP application 2017-159153.
A Third Office Action dated Apr. 3, 2017, in corresponding Japanese Application No. 2013-558270, and English translation thereof (8 pages).
Further Examination Report dated Apr. 29, 2019 in corresponding New Zealand Application No. 740448 (2 pages).
Second Office Action issued in corresponding Chinese Application No. 2016-109065994 dated Jan. 2, 2019, with English translation, (15 pages).

(56) References Cited

OTHER PUBLICATIONS

Final Office Action issued in corresponding Japanese Application No. 2017-159153 dated Feb. 15, 2019, with English translation, (8 pages).
First Office Action issued in corresponding Japanese Application No. 2017-159153 dated Jul. 23, 2018, with English translation, (11 pages).
A Further Examination Report dated May 25, 2018, in a corresponding New Zealand Patent Application No. 740448 (3 pages).
A Communication Pursuant to Article 94(3) EPC dated May 14, 2018, in a corresponding European Patent Application No. 12 757 502.5 (5 pages).
A First Office Action dated Apr. 4, 2018, in a corresponding Chinese Patent Application No. 201610906599.4 (10 pages), and an English translation thereof (8 pages).
A First Examination Report dated Apr. 3, 2018, in a corresponding New Zealand Patent Application No. 740448 (3 pages).
A Further Examination Report dated Jan. 19, 2018, in a corresponding New Zealand Patent Application No. 724101 (2 pages).
A Further Examination Report dated Dec. 4, 2017, in a corresponding New Zealand Patent Application No. 724101 (2 pages).
Notice of Reasons for Rejection dated Jul. 28, 2016 in a corresponding Japanese Application No. 2013-558270 (8 pages) and an English translation thereof (12 pages).
Office Action dated Feb. 1, 2016 in a corresponding Japanese Patent Application No. 2013-558270 (10 pages) and an English translation thereof (10 pages).
Second Office Action dated Nov. 11, 2015 in a corresponding Chinese Patent Application No. 201280013648.1 (6 pages), and an English translation thereof (8 pages).
Patent Examination Report No. 1 dated Jul. 22, 2014 in corresponding Australian Patent Application No. 2012229885.
First Examination Report dated Apr. 17, 2014 in corresponding New Zealand Patent Application No. 615269.
International Search Report for International Patent Application PCT/AU2012/000269 dated May 31, 2012.
First Examination Report dated Sep. 28, 2016, in a corresponding New Zealand Application No. 724101 (2 pages).
First Examination Report dated Mar. 16, 2015 in a corresponding New Zealand Patent Application No. 705724 (2 pages).
Further Examination Report dated May 20, 2015 in a corresponding New Zealand Patent Application No. 615269 (2 pages).
Office Action issued in corresponding Chinese Appln. No. 201280013648.1 dated Mar. 24, 2015 (7 pages) and English translation (10 pages).
Extended European Search Report dated Nov. 17, 2014 issued in corresponding European Patent Application No. 12757502.5 (7 pages).
A Third Office Action dated Apr. 3, 2017, in a corresponding Japanese Application No. 2013-558270 (3 pages), and an English translation thereof (5 pages).
Japanese Office Action for Application No. 2021-547237, three pages, dated Nov. 27, 2023.

* cited by examiner

AIR DELIVERY CONDUIT

CROSS-REFERENCE TO APPLICATION

This application is a continuation application of U.S. application Ser. No. 16/912,857, filed Jun. 26, 2020, now U.S. Pat. No. 11,565,071, which is a continuation application of U.S. application Ser. No. 15/599,889, filed May 19, 2017, now U.S. Pat. No. 10,729,869, which is a divisional application of U.S. application Ser. No. 14/005,094, filed Sep. 13, 2013, now U.S. Pat. No. 9,656,038, which was the U.S. national phase of International Application No. PCT/AU2012/000269 filed Mar. 15, 2012, which designated the U.S. and claims priority to Australian Provisional Application No. AU 2011900911 filed Mar. 15, 2011, the entire contents of each of which are hereby incorporated by reference.

FIELD OF TECHNOLOGY

The present technology relates to air delivery conduits used in Positive Airway Pressure (PAP) systems for treatment, e.g., of Sleep Disordered Breathing (SDB), such as Obstructive Sleep Apnea (OSA), with Continuous Positive Airway Pressure (CPAP) or Non-Invasive Positive Pressure Ventilation (NIPPV).

BACKGROUND OF TECHNOLOGY

PAP systems to deliver breathable gas to a patient typically include a PAP device, an air or gas delivery conduit, and a patient interface. In use, the air delivery conduit delivers pressurized air or gas from the PAP device to the patient interface in contact with the patient's face.

The present technology provides improvements to known air delivery conduits.

SUMMARY OF TECHNOLOGY

One aspect of the disclosed technology relates to an air delivery conduit having increased comfort and visual appeal.

Another aspect of the disclosed technology relates to an air delivery conduit comprising a textile.

Another aspect of the disclosed technology relates to an air delivery conduit that is quiet, unobtrusive and/or appealing to consumers, and includes a textile.

Another aspect of the disclosed technology is an air delivery conduit for use with a facial mask which is constructed and arranged to lengthen or contract without twisting or disrupting a seal of the facial mask.

Another aspect of the disclosed technology relates to an air delivery conduit including a textile that has a first elasticity in a first direction and a second elasticity in a second direction.

Another aspect of the disclosed technology relates to an air delivery conduit including a textile that is made airtight.

Another aspect of the disclosed technology relates to an air delivery conduit comprising a textile, the air delivery conduit having a smooth inner surface.

Another aspect of the disclosed technology relates to an air delivery conduit comprising a textile, the air delivery conduit having a reinforcing structure, e.g., to provide some level of crush resistance, which reinforcing structure may take the form of a continuous member (e.g., a helix) or a discontinuous member or members (e.g., a linear, curved, or zig-zag stiffener provided along the conduit).

Another aspect of the disclosed technology relates to an air delivery conduit comprising a textile having an airtight arrangement and a reinforcing structure.

Another aspect of the disclosed technology relates to an air delivery conduit comprising a textile, the textile having a warp and a weft, and the warp and the weft are arranged to maximize the stretch of the air delivery conduit in a first direction.

Another aspect of the disclosed technology relates to an air delivery conduit comprising a textile, the textile having a warp and a weft, and the warp and the weft are arranged to minimize the torque of the air delivery conduit in a second direction.

Another aspect of the disclosed technology relates to an air delivery conduit comprising a textile, the air delivery conduit having a spiral or helix, the air delivery conduit having a first end attachable to a mask.

Another aspect of the disclosed technology relates to an air delivery conduit having a spiral or helix, the air delivery conduit having a first end attachable to a mask and a second end attachable to a flow generator.

Another aspect of the disclosed technology relates to an air delivery conduit comprising a textile, the air delivery conduit having a spiral or helix, the air delivery conduit having a first end, the first end having a first inner diameter and attachable to a mask, and a second end having a second inner diameter and attachable to a flow generator.

Another aspect of the disclosed technology relates to an air delivery conduit having reduced intrusiveness and greater appeal to consumers due to the use of fabric, thereby increasing compliance rates.

Another aspect of the disclosed technology relates to an air delivery conduit that is lighter as fabric may be lighter than typical plastics, thereby reducing the effects of the air delivery conduit drag at the interface.

Another aspect of the disclosed technology relates to an air delivery conduit having a textile that is able to shear thereby reducing the torque of the air delivery conduit and hence reducing the air delivery conduit drag forces. This in turn creates a more stable mask seal and more effective treatment.

Another aspect of the disclosed technology relates to an air delivery conduit that is more supple as the warp and weft of the textile have been formed to improve the flexibility and extensibility of the air delivery conduit. The suppleness reduces the air delivery conduit drag and also increases the usability of the air delivery conduit.

Another aspect of the disclosed technology relates to an air delivery conduit that reduces conduit drag on a mask compared to prior art conduits which may impart substantial torque to a mask which may cause the mask seal to leak.

Another aspect of the disclosed technology relates to an air delivery conduit that may reduce the need for an additional swivel component which may otherwise be required to be placed inline between the air delivery conduit and a mask, or between the air delivery conduit and a flow generator.

Another aspect of the disclosed technology relates to an air delivery conduit comprising a textile (e.g., helically wound) forming a tubular member adapted to deliver pressurized air, the textile including a warp and a weft (or a machine direction and a transverse direction), wherein characteristics of the warp and the weft are selected to provide the tubular member with a selected stiffness to at least partially counteract twisting of the tubular member about its longitudinal axis.

Another aspect of the disclosed technology relates to an air delivery conduit comprising a textile (e.g., helically wound) forming a tubular member adapted to deliver pressurized air, the textile including a warp and a weft (or a machine direction and a transverse direction), wherein characteristics of the warp and the weft are selected to provide the tubular member with desired features in relation to stretching (e.g., along the longitudinal axis of the tubular member) and/or to at least partially counteract or compensate for twisting about the longitudinal axis.

Another aspect of the disclosed technology relates to a mask assembly for treating sleep disordered breathing, comprising an air delivery conduit according to an example of the disclosed technology; and a patient interface in communication with the conduit.

Another aspect of the disclosed technology relates to a method of forming an air delivery conduit. The method comprises providing a material in an at least partially molten state to form a tubular member to deliver pressurized air; and curing the material into a hardened state, wherein during the curing step a fabric is attached to an outer surface of the material so as to fuse the material and the fabric.

Another aspect of the disclosed technology relates to a method of forming an air delivery conduit. The method comprises forming a laminated fabric sheet including an inner laminate layer and an outer fabric layer; and welding opposing end portions of the laminated fabric sheet to form a tubular conduit having a longitudinal weld seam.

Another aspect of the disclosed technology relates to a method of forming an air delivery conduit. The method comprises providing a tubular member to deliver pressurized air; providing a fabric to cover the tubular member; and molding a cuff to the tubular member, wherein the fabric is fused with the cuff during the molding step.

Another aspect of the disclosed technology relates to a method of forming an air delivery conduit. The method comprises laminating, coating or otherwise adding a polymer to a fabric sheet; and forming the fabric sheet into a tubular shape thereby forming a conduit to deliver pressurized air, wherein the laminated polymer provides form to the conduit.

Other aspects, features, and advantages of the disclosed technology will become apparent from the following detailed description when taken in conjunction with the accompanying drawings, which are a part of this disclosure and which illustrate, by way of example, principles of this technology.

BRIEF DESCRIPTION OF THE DRAWINGS

The accompanying drawings facilitate an understanding of the various embodiments of the technology. In such drawings:

FIG. 2-1 is a side view of an air delivery conduit according to an example of the disclosed technology;

FIG. 2-2 is a partial perspective view of the air delivery conduit of FIG. 2-1;

FIG. 2-3 is a cross-sectional view along the line 2-3-2-3 in FIG. 2-2;

FIG. 2-4 is a cross-sectional view of an air delivery conduit according to another example of the disclosed technology along a line similar to the line 2-3-2-3 in FIG. 2-2;

FIG. 2-5 is a cross-sectional view of an air delivery conduit according to another example of the disclosed technology along a line similar to the line 2-3-2-3 in FIG. 2-2;

FIG. 3 is a cross-sectional view of an air delivery conduit according to an example of the disclosed technology;

FIG. 4 is a front end view of an air delivery conduit according to an example of the disclosed technology;

FIG. 5 is a side view of an air delivery conduit and cuff according to an example of the disclosed technology;

DETAILED DESCRIPTION OF ILLUSTRATED EXAMPLES

The following description is provided in relation to several examples (most of which are illustrated, some of which may not) which may share common characteristics and features. It is to be understood that one or more features of any one example may be combinable with one or more features of the other examples. In addition, any single feature or combination of features in any of the examples may constitute additional examples.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen. The respiratory therapy devices or blowers described herein may be designed to pump fluids other than air.

One or more examples may include exemplary dimensions. Although specific dimensions and ranges may be provided, it is to be understood that these dimensions and ranges are merely exemplary and other dimensions and ranges are possible depending on application. For example, ranges that vary from those provided, e.g., up to or more than, +/−10% may be suitable for particular applications.

1. PAP System

A PAP system (e.g., CPAP system) typically includes a PAP device (including a blower for generating air at positive pressure), an air delivery conduit (also referred to as a tube or tubing), and a patient interface (e.g. a mask) adapted to form a seal with the patient's face. In use, the PAP device generates a supply of pressurized air (in the range of 2-40 cm $H_2O$, approximately 8-12 cm $H_2O$ for OSA treatment) that is delivered to the patient interface via the air delivery conduit. The patient interface or mask may have suitable configurations as is known in the art, e.g., full-face mask, nasal mask, oro-nasal mask, mouth mask, nasal prongs, nozzles, cradle, etc. Also, headgear may be utilized to comfortably support the patient interface in a desired position on the patient's face.

2. Mask System

In an example, a mask system may include a frame, a cushion and headgear. The frame may anchor the cushion in position and allow for attachment of the headgear. The frame may be a rigid or semi rigid component. The cushion may seal with the patient's face in order to provide therapy to the patient. The cushion may be a flexible element. The headgear may stabilize and support the frame and cushion in position on the patient's face when in use. The headgear may be a flexible or semi rigid element, or a combination thereof, and may be constructed of fabric, for example.

Figure 1:
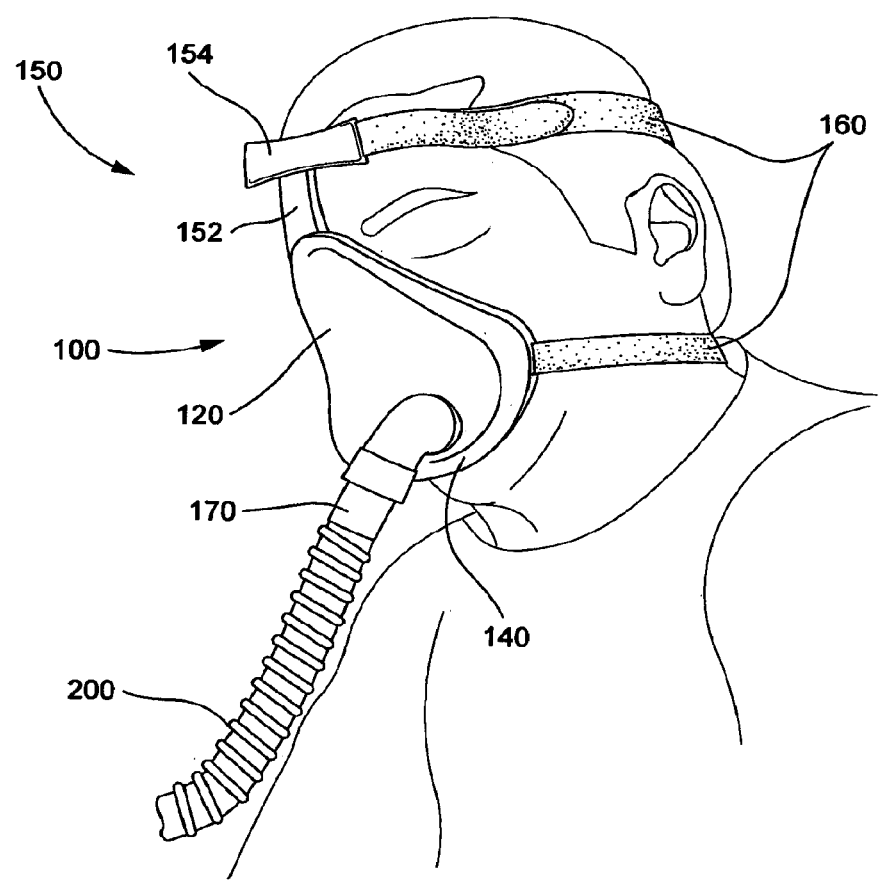
FIG. 1 is a mask system according to an example of the disclosed technology.

FIG. 1 illustrates a mask system 100. The mask system 100 includes a frame 120, a cushion 140 and headgear 160. The frame 120 anchors the cushion 140 in position. The frame 120 may be a rigid or semi rigid component constructed of, for example, polycarbonate. The cushion 140 may be a flexible element constructed of, for example, silicone to provide a comfortable fit to the patient.

The mask system 100 may include a forehead support 150 and an elbow 170. The forehead support 150 may include a beam 152 and at least one forehead pad 154. The beam 152 may extend between the frame 120 and the forehead pad 154. The forehead pad may rest on the patient's forehead and receive a headgear 160.

The elbow 170 includes a first end that interfaces with an aperture in the frame 120, and a second end adapted to connect to an air delivery tube 200. Tube 200 may connect or sealingly engage with a flow generator that delivers pressurized breathable gas to the patient.

The headgear 160 is adapted to secure the mask system 100 to the patient's face. The headgear 160 may connect to the frame 120 and/or forehead pad 154 via an attachment device, e.g., clips, loops or other such devices. Further, an air delivery conduit 200 may be connected to the elbow to supply pressurized air to the mask.

3. Air Delivery Conduit

Figures 1, 2:
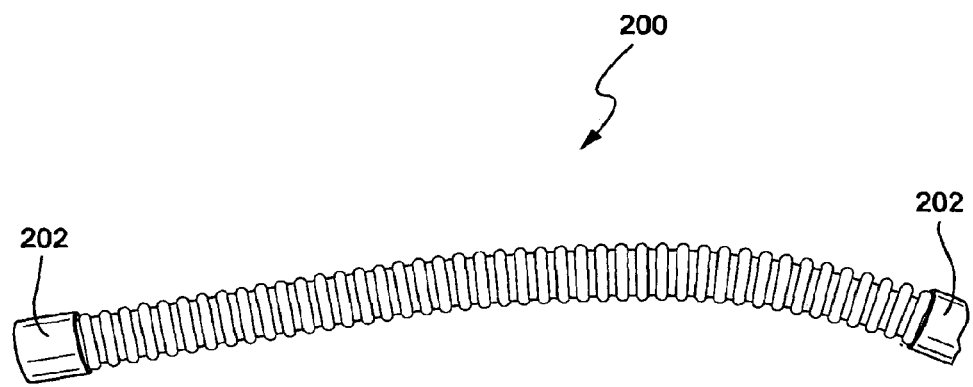
Figure 2:
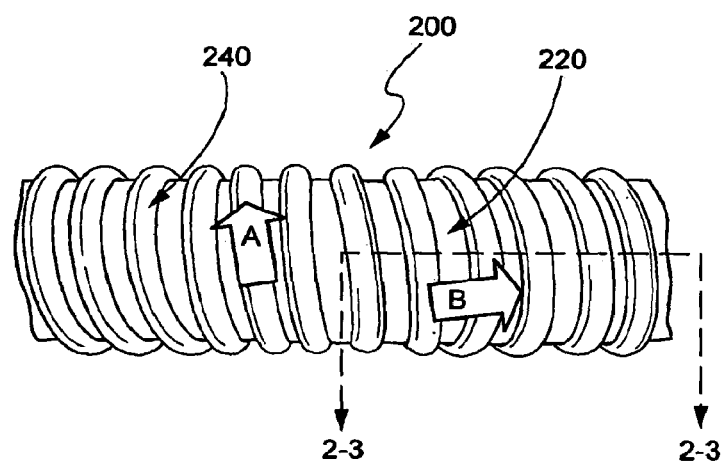
Figures 2, 3:
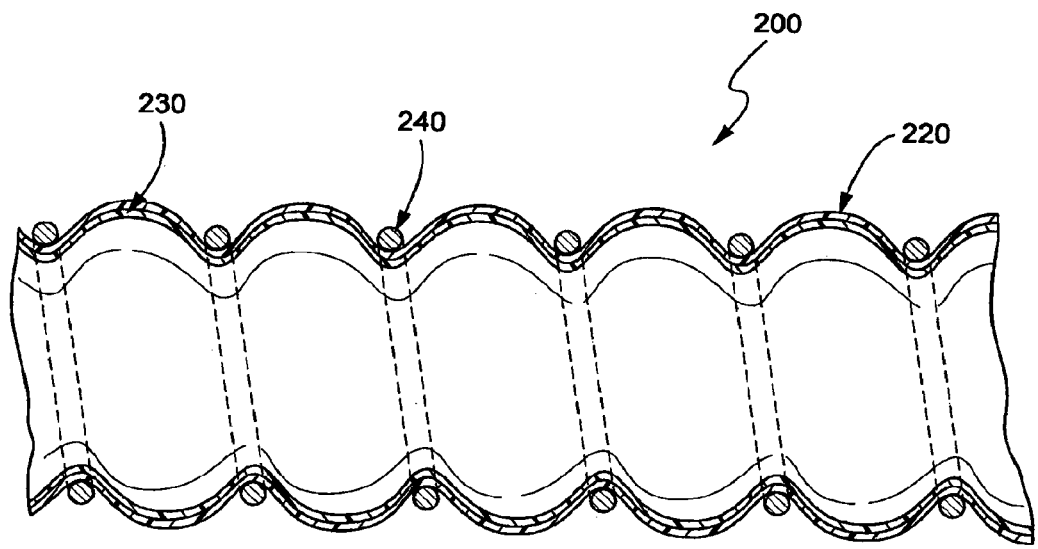

FIGS. 2-1 to 2-3 illustrate an air delivery conduit 200 according to an example of the disclosed technology. The air delivery conduit 200 may comprise an outer textile or fabric layer 220, an inner laminate layer 230 and a support structure 240 attached to an outer surface of the textile 220.

The air delivery conduit 200 may be generally cylindrical although alternative shapes may be possible also, for example, oval, square, etc. The textile 220 may be woven, non-woven, spacer fabric, knitted, braided or 3-D printed, for example. The textile 220 may be formed from a planar piece of material that is wrapped and joined along a longitudinal axis to create a tubular or other shape. The textile layer 220 may be formed by winding a textile sheet around a central axis in a helical arrangement to form a tubular configuration. The air delivery conduit 200 may include cuffs 202 for attachment to an air supply source and/or a mask.

Additionally, the textile 220 may be formed in one piece by weaving, knitting or braiding, for example. Also, the textile itself and other components of the air delivery conduit may be assembled or joined by lamination, welding, gluing, stitching, kitting, etc.

The textile may be arranged to have increased or reduced elasticity, stretchability or stiffness in certain directions. For example, the threads or fibres of the textile may have varying elasticities or stiffnesses and the elasticities (or level of stiffness) may be selected to provide increased or reduced elasticity, stretchability or stiffness of the textile in certain directions. These directions may include, for example, the directions of the warp and weft of a woven textile, the warp direction and the weft direction of a knitted textile, and the machine direction and the transverse direction of other textiles (e.g., nonwoven).

In the example of a woven textile, the textile 220 may include a warp and a weft. The warp corresponds to the fibers or threads running along the length of the material. The weft corresponds to the fibers or threads running along the width of the material. Therefore, the warp of the textile 220 may be parallel to the central axis of the air delivery conduit 200. The weft of the textile conduit 220 may correspond to the circumference of the air delivery conduit 200.

However, if the textile 220 is wound about in a helical arrangement, the warp of the textile 220 may be arranged to follow the helix and the weft may be arranged along the longitudinal axis of the conduit, as shown in FIG. 2-2. In FIG. 2-2, the arrow A corresponds to the helix of the textile and represents the warp, and the arrow B is in the direction of the longitudinal axis of the conduit and represents the weft.

The warp and the weft may comprise different fibers or threads. For example, the weft may be formed of a material that has more stretch or is more elastic than the warp. In this configuration, the textile 220 may be able to stretch more readily in a lengthwise direction, i.e. along its central axis due to the elasticity or stretchiness of the weft. The textile 220 also may more readily stretch when the conduit is bent, due to the increased stretchability of the weft. This may cause the air delivery conduit 200 to be more supple or more readily deform and thereby reduce conduit drag.

Furthermore, the textile 220 in this arrangement may exhibit an increased resistance to torque or twisting when the air delivery conduit 200 is pulled or a lengthwise force is applied to the air delivery conduit, due to the less elastic material of the warp. Rather, the textile 220 may shear to absorb the force. This behavior is unlike conventional extensible air delivery conduits (for example, some plastic air delivery conduits) that twist when they are extended or pulled lengthwise. Conventional extensible air delivery tubes may comprise a web and a support structure (or helix) wound around a central axis to form the tube. The web and helix may be formed from materials that are not intended to be extensible under normal loading conditions for sleep apnea therapy. Thus, when the tubes are pulled along their axis, the helix attempts to straighten out, but since the helix is wound, it twists. Since the web is substantially inextensible, the web will twist with the helix thereby causing the whole tube to twist. Accordingly, in an example of the disclosed technology, the warp and weft may be arranged to resist such twisting.

A further advantage of the warp having little to no stretch or elasticity is that the conduit may be formed to have a more uniform configuration. That is, when the conduit is formed, the textile is wound around the central axis and since the warp has little elasticity, the material is less likely to deform when wound, thus creating a more uniform air delivery conduit.

In another example, the warp may be formed of a material that has more stretch or is more elastic than the weft. In this configuration, the textile 220 may have limited to no ability to stretch lengthwise or along its central axis due to the lack of elasticity of the weft. The limited stretchiness or elasticity of the weft may also limit the ability for the textile 220 and thus the conduit 200 to bend or curve. This may be desirable when a position of the air delivery conduit is to remain stable, such as in the case of an air delivery conduit that is secured on the patient's head or night gown. Furthermore, as the warp has a higher elasticity, the air delivery conduit may exhibit a reduced resistance to torque or twisting or may readily torque or twist, for example when pulled or a lengthwise force is applied.

The inner laminate layer 230 may be formed on an inner surface of the textile 220, as shown in FIGS. 2-3 to 2-5. The inner laminate 230 may prevent air from leaking through the fibers of the textile 220. The inner laminate 230 may be glued, melted, sprayed or otherwise formed on the textile 220. The inner laminate may also be embodied as part of the textile and may react, to heat for example, to form a sealing layer on the textile 220. For example, the inner laminate could form a heat-activated adhesive backing of the textile 220 that once activated could form a sealing layer. The inner laminate could be activated as the textile is wound to form a tubular shape or could be activated once the entire textile is arranged in the tubular shape. Further, the laminate 230 may be formed from polyurethane, silicone, nylon or other flexible, substantially impermeable materials.

It is noted that the textile 220 may not require a laminate to make the air delivery conduit airtight. For instance, the textile 220 may be sufficiently impervious to air flow, or otherwise airtight, e.g., the textile may include a canvas.

As shown in FIGS. 2-3 to 2-5, support structure 240 may form a helix, and may further be constructed to form a spring. However, the support structure may include other configurations, e.g., a series of rings along the length of the textile. Generally, the support structure provides form to the conduit. That is, the conduit will adopt the shape of the support structure. The support structure also provides crush-resistance to the conduit, while maintaining flexibility of the conduit. The support structure 240 may be formed of a resilient material having sufficient hardness to maintain the air delivery conduit 200 in an open position should the air delivery conduit 200 be subjected to a compression force. For example, if the patient were to lie on the air delivery conduit, the air delivery conduit would remain patent or at least partially open. The support structure 240 may be formed from nylon, polypropylene, high durometer silicone (e.g. 80 Shore A), metal or other suitable materials. The support structure 240 may provide structural integrity to the air delivery conduit, and may further permit flexibility lengthwise and rotationally.

Preferably, the air delivery conduit 200 has a smooth inner surface. The smooth inner surface may be formed by the inner laminate 230. The smooth inner surface provides an advantage over air delivery conduits having corrugations or steps as the air travelling through the air delivery conduit 200 has a lower impedance because the airflow is not interrupted by undulations, steps or corrugations in the conduit wall. Furthermore, the air delivery conduit 200 may have a lower noise output as the airflow can travel along the air delivery conduit with less turbulence because the air does not collide with steps, corrugations or undulations in the conduit side wall.

In an example, the air delivery conduit 200 may have a length in the range of about 200-700 mm, preferably about 200-400 mm, and more preferably about 300 mm. Further, the length of the air delivery conduit may be greater than 200 mm.

In another example, the air delivery conduit 200 may have a length that is at least 1000 mm, preferably 2000 mm. Further, the air delivery conduit 200 may have a length that is greater than 2000 mm.

In another example of the disclosed technology, an air delivery conduit 200-1 may comprise a textile layer 220-1, an inner laminate layer 230-1, an outer laminate layer 234-1 and a support structure 240-1.

The air delivery conduit 200-1 is similar to the air delivery conduit 200 described above, except for the inclusion of the outer laminate layer 234-1.

The outer laminate 234-1 may be formed on an outer surface of the textile 220-1 and may also cover the support structure 240-1. The outer laminate 234-1 may prevent air from leaking through the fibers of the textile 220-1 and may also protect the support structure 240-1. The outer laminate 234-1 may also provide structural integrity or stiffness to the air delivery conduit 200-1 to assist in preventing occlusion of the air delivery conduit. The outer laminate 234-1 may be glued, melted, sprayed or otherwise formed on the textile 220-1. The outer laminate 234-1 may comprise a fabric or other soft conformable material to enhance patient comfort and visual appeal. The outer laminate 234-1 may be polyurethane, silicone, nylon or other flexible, substantially impermeable materials.

Alternatively, as shown in FIG. 2-5, an air delivery conduit 200-2 may include an outer laminate 234-2 disposed between a textile 220-2 and a support structure 240-2 such that support structure 240-1 is the outer most portion of the air delivery conduit 200-2. It is noted that the outer laminate 234-2 may also be embodied as part of the textile 220-2 as described above with regard to the inner laminate 230. An inner laminate 230-2 may be formed on an inner surface of the textile 220-2.

In another example of the disclosed technology, the textiles may be replaced with a polymer or composite structure having a different elasticity in different directions, e.g. axial and radial directions. Preferably the air delivery conduit is elastic and stretches along its length with little torque as it expands or contracts along its length. In one form, a post-processing step may be used, e.g. temperature annealing, to impart differential axial and radial elasticity.

3.1 Fused Tube and Fabric

In an example of the disclosed technology, shown in FIG. 3, a textile 310 may be fused to a tubular member 302 to form an air delivery conduit 300. For example, the tubular member may comprise a plastic material formed by an extrusion process. After the tubular member 302 is extruded and while the tubular member is in at least a partially molten state, the textile 310 is wound around the tubular member. As the tubular member hardens, the textile 310 is fused to the tubular member 302, thus providing a softer, more visually appealing outer surface to the air delivery conduit 300, which may enhance comfort to the patient and/or increase patient compliance.

The textile may be a fabric, ribbon, or other soft material. The textile 310 may further comprise a composite material, e.g., a fabric outer layer and an adhesive inner layer to adhere to the tubular member 302.

The textile may be helically wound around the tubular member, and may comprise any textile configuration described in other examples of the disclosed technology. For example, the stiffness of the tubular member 302 and therefore the air delivery conduit may be increased in a selected direction by a textile thread or material that extends in the selected direction and has a higher stiffness than the material of the tubular member 302.

3.2 Fabric with Fusion Zone

Figures 2, 3, 4:
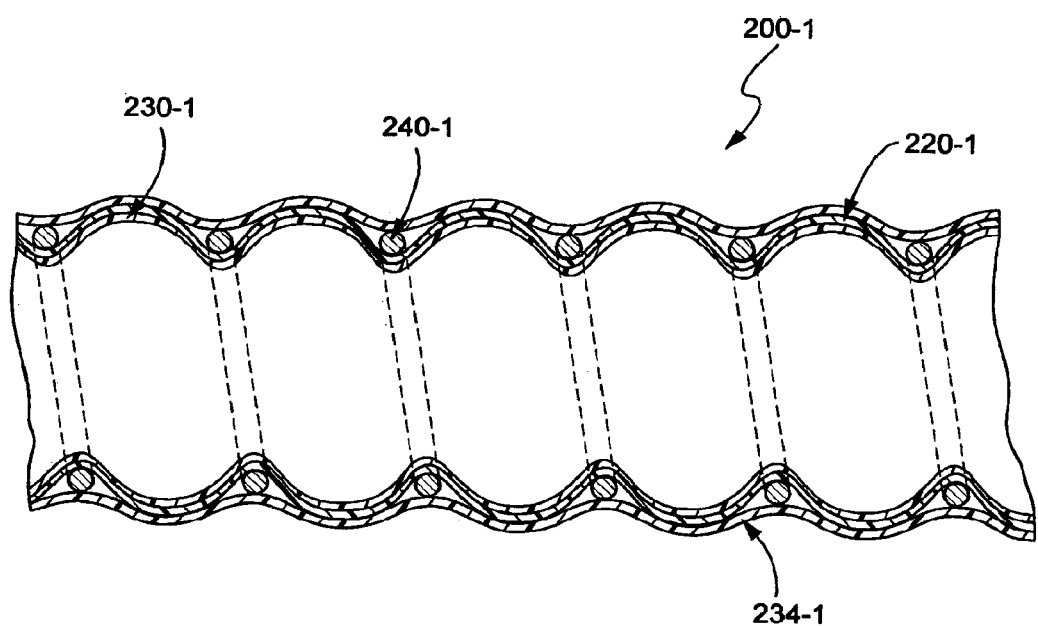

A laminated fabric sheet may be formed into a tubular shape and welded along a longitudinal axis to form an air delivery conduit 400 having a fusion zone 442, as shown in FIG. 4. The laminated fabric sheet may comprise a textile layer 420 and an inner laminate 430.

The laminated fabric sheet may be welded using a filler material such as a thermoplastic material or adhesive. The filler material may be the same material as the laminate 430. The filler material may more readily fuse to the textile 420 and the laminate 430 if the filler material and the laminate comprise the same material, or are at least chemically compatible.

The fusion zone may be configured to be flexible to allow the air delivery conduit 400 to bend and conform to the patient's movement while sleeping. The material of the laminated fabric sheet and/or the filler material in the fusion zone may be a flexible material such as a TPE, nylon, polypropylene, silicone and hence may maintain or increase the flexibility of the tube in this region. Alternatively, a stiffer material may be used but may have a geometry that permits or enhances flexibility e.g. thin regions. The fusion zone may also be stretchable along its length to accommodate stretching of the air delivery conduit 400. The textile 420 may comprise any textile configuration described in other examples of the disclosed technology.

3.3 Molded Cuff and Textile Cover

Figures 2, 3, 4, 5:
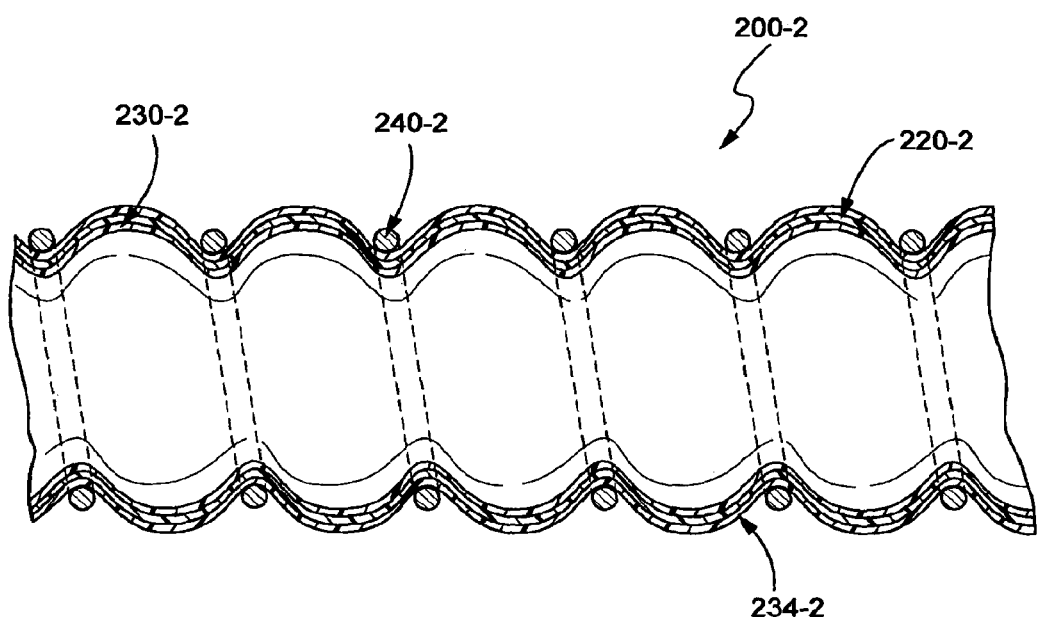
Figure 3:
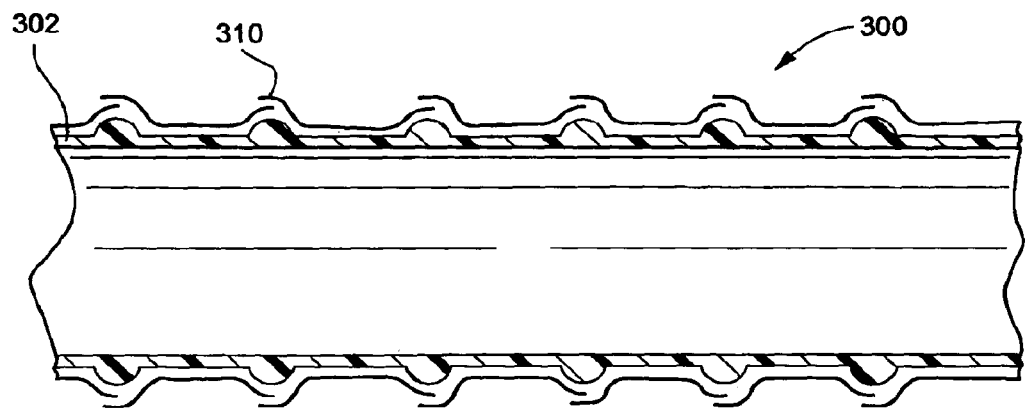
Figure 4:
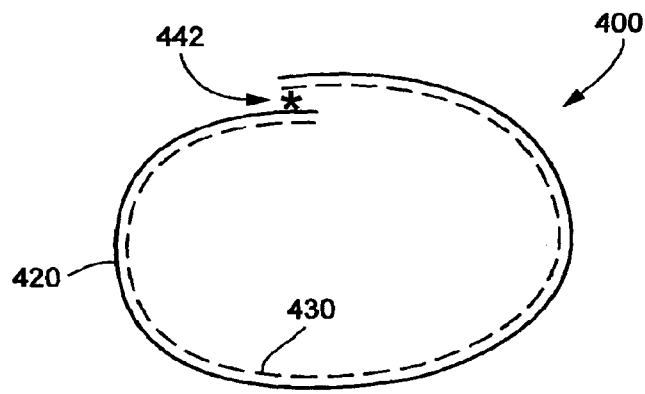
Figure 5:
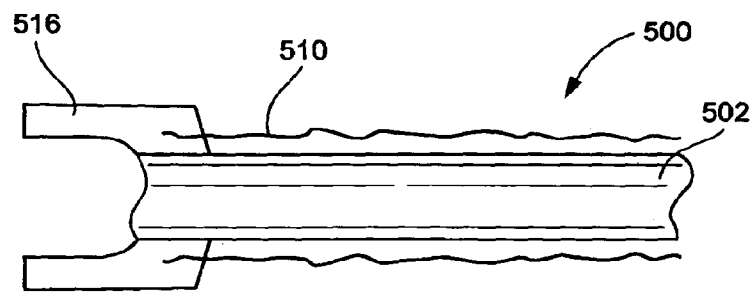

In an example of the disclosed technology, shown in FIG. 5, a textile 510 may cover a tubular member 502 to form an air delivery conduit 500. For example, the tubular member may comprise a plastic material formed by an extrusion process. After the tubular member 302 is extruded, the tubular member and the textile 510 may be placed in a tool used to mold a cuff 516. Thus, the cuff 516 may be molded directly onto the tubular member 502 and the textile 510 may be molded into the cuff so as to form a space between the textile 510 and the tubular member 502. The textile cover provides a softer, more visually appealing outer surface to the air delivery conduit 500, which may enhance patient comfort and/or increase patient compliance.

Longitudinal end portions of the textile 510 may be welded to form a longitudinal seam thereby sealing the textile to prevent debris and bacteria from collecting inside the textile cover.

The cuff 516 may be formed at both ends of the air delivery conduit and may also function to connect the air delivery conduit to a mask or an air supply source. The cuff may be formed from a polymer such as silicone, thermoplastic, nylon or other suitable materials.

In this example, the warp (i.e. the yarn along the length of the tube) may be more elastic or stretchable than the weft in order to allow the tube to stretch along its length.

3.4 Reinforced Textile Conduit

Figure 6:
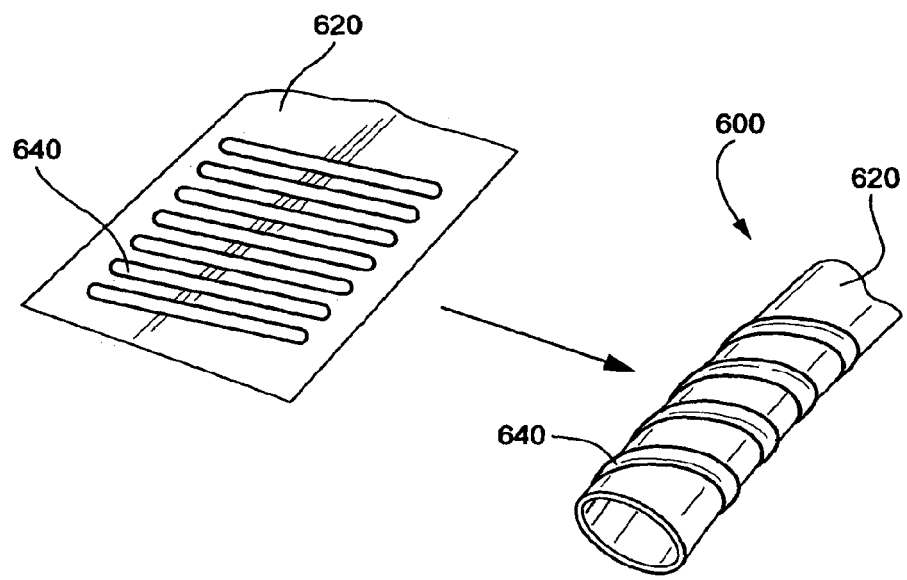
FIG. 6 illustrates a process of forming an air delivery conduit according to another example of the disclosed technology.

A textile 620 in sheet form may be provided with a laminated polymer which functions as a support structure 640 when the sheet is formed into a tubular shape thereby forming an air delivery conduit 600, as shown in FIG. 6. The support structure may be laminated as lines, crosses, or other shapes to provide form to the conduit (e.g., the conduit will adopt the shape of the support structure) and encourage the conduit to maintain a tubular shape, thereby preventing occlusion. In the illustrated example, the polymer is laminated as diagonal lines across the textile sheet. When the sheet is formed into a tubular shape, the diagonal lines form helixes.

The support structure 640 may be formed of a material having sufficient hardness to maintain the conduit 600 in an open position under its own weight. Preferably, the hardness of the material may also main the conduit in an open position should the conduit be subjected to a compression force, e.g., from the patient's head. The support structure 640 may further include a shape or configuration that promotes or restricts bending in certain areas.

The ends of the textile sheet may be welded (e.g., ultrasonic welded) to form the tubular shape. The textile 620 may have an inner laminate layer to form an air seal.

Figure 7:
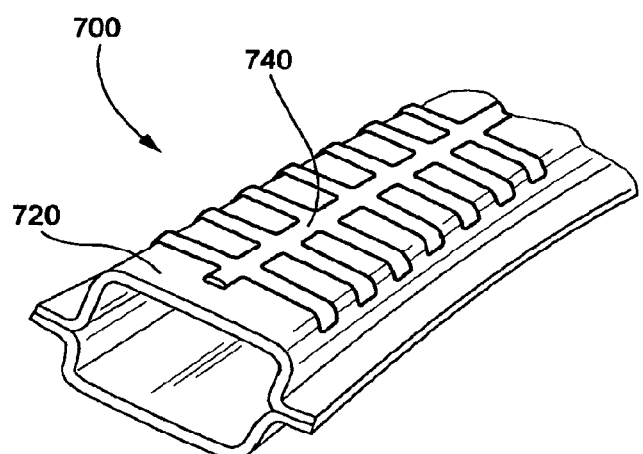
FIG. 7 is a partial perspective view of an air delivery conduit according to another example of the disclosed technology.

In an example shown in FIG. 7, an air delivery conduit 700 includes a textile 720 having a support structure 740 formed thereon. The support structure 740 has a skeleton configuration; however, other configurations may be suitable, as mentioned above. The support structure 740 may be provided along the length of the conduit to provide form and encourage the conduit to maintain a tubular shape. The support structure may be provided along a seam of the fabric, such as the fusion zone described above.

While the technology has been described in connection with several examples, it is to be understood that the technology is not to be limited to the disclosed examples, but on the contrary, is intended to cover various modifications and equivalent arrangements included within the spirit and scope of the technology. Also, the various examples described above may be implemented in conjunction with other examples, e.g., one or more aspects of one example may be combined with one or more aspects of another example to realize yet other examples. Further, each independent feature or component of any given assembly may constitute an additional example. In addition, while the technology has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. An air delivery conduit configured to connect a patient interface to a supply of pressurized breathable gas for delivery of the breathable gas to a patient for treatment of sleep disordered breathing, the air delivery conduit comprising:
    an inner surface defining a tubular passageway configured to, in use, convey the breathable gas from the supply to the patient interface;
    an outer surface having a tubular shape and being exposed to atmosphere in use; and
    at least one resilient support structure attached to the outer surface and extending around a circumference of the conduit such that, in an axial cross-sectional view of the conduit, the inner surface and the outer surface extend between spaced-apart sections of the support structure, the support structure being configured to provide form and crush-resistance to the conduit during treatment of sleep disordered breathing,
    wherein, in the axial cross-sectional view, the inner surface and the outer surface have matching arc-shaped portions extending between adjacent spaced-apart sections of the support structure, each arc-shaped portion of the inner surface forming a concave shape and each arc-shaped portion of the outer surface forming a convex shape, and
    wherein the outer surface has a substantially non-circular transverse cross-sectional shape.

2. The air delivery conduit of claim 1, wherein the support structure comprises a plurality of rings positioned along the length of the outer surface to support and provide form to the conduit.

3. The air delivery conduit of claim 1, wherein the inner surface is formed of an air impermeable material and the outer surface comprises a textile material, wherein the support structure is attached to the textile material.

4. The air delivery conduit of claim 3, wherein the support structure is laminated to the textile material.

5. The air delivery conduit of claim 4, wherein the support structure is laminated as a series of discontinuous lines.

6. The air delivery conduit of claim 5, wherein the discontinuous lines form a plurality of rings disposed along a length of the conduit.

7. The air delivery conduit of claim 5, wherein the discontinuous lines are diagonal lines.

8. The air delivery conduit of claim 3, wherein the textile material is woven, non-woven, braided or three-dimensionally printed.

9. The air delivery conduit of claim 3, wherein the air impermeable material comprises polyurethane, silicone, or nylon.

10. The air delivery conduit of claim 3, wherein the air delivery conduit comprises an inner laminate layer formed of the air impermeable material and a textile layer formed of the textile material.

11. The air delivery conduit of claim 10, wherein the laminate layer is glued, melted, or sprayed on the textile layer.

12. The air delivery conduit of claim 1, wherein the support structure comprises a polymer.

13. The air delivery conduit of claim 12, wherein the polymer comprises nylon, polypropylene, or silicone.

14. The air delivery conduit of claim 1, further comprising a first cuff attached to a first end of the conduit and a second cuff attached to a second end of the conduit.

15. The air delivery conduit of claim 14, wherein the first cuff is configured to facilitate connection of the conduit to the patient interface, and the second cuff is configured to facilitate connection of the conduit to the supply of pressurized breathable gas.

16. The air delivery conduit of claim 1, wherein the conduit has an inner surface that is smooth.

17. The air delivery conduit of claim 1, wherein the inner surface is formed of an air impermeable material and the outer surface comprises a textile material
further comprising a first cuff attached to a first end of the conduit and a second cuff attached to a second end of the conduit,
wherein the first cuff is configured to facilitate connection of the conduit to the patient interface, and the second cuff is configured to facilitate connection of the conduit to the supply of pressurized breathable gas,
wherein the support structure comprises a plurality of rings positioned along the length of the outer surface to support and provide form to the conduit,
wherein the support structure is attached to the textile material,
wherein the support structure comprises a polymer,
wherein the air impermeable material comprises polyurethane, silicone or nylon, and
wherein the conduit has a length of between 200 mm and 700 mm.

18. A mask assembly for providing pressurized gas to a patient for treatment of sleep disordered breathing, the mask assembly comprising:
a patient interface configured to interface with the patient's face to deliver a flow of pressurized gas to the patient's airways; and
the air delivery conduit of claim 1.

19. The air delivery conduit of claim 1, wherein each of the inner surface and the outer surface is constructed of a flexible air impermeable material.

20. The air delivery conduit of claim 19, wherein both the inner surface and the outer surface do not comprise a textile material.

21. The air delivery conduit of claim 1, wherein the air delivery conduit comprises an inner air impermeable laminate layer having the inner surface and an outer air impermeable laminate layer having the outer surface, and wherein a textile layer is disposed between the inner laminate layer and the outer laminate layer.

* * * * *